US006291480B1

(12) United States Patent
Biftu et al.

(10) Patent No.: US 6,291,480 B1
(45) Date of Patent: Sep. 18, 2001

(54) DIARYL PIPERIDYL PYRROLE DERIVATIVES AS ANTIPROTOZOAL AGENTS

(75) Inventors: Tesfaye Biftu, Westfield; Danqing Dennis Feng, Branchburg Township; Gui-Bai Liang, Scotch Plains; Mitree M. Ponpipom, Branchburg, all of NJ (US); Xiaoxia Qian, New York, NY (US); Michael H. Fisher, Ringoes; Matthew J. Wyvratt, Mountainside, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/710,147

(22) Filed: Nov. 10, 2000

Related U.S. Application Data
(60) Provisional application No. 60/165,142, filed on Nov. 12, 1999.

(51) Int. Cl.$^7$ .......................... C07D 401/04; A61K 31/44
(52) U.S. Cl. ............................................. 514/318; 546/194
(58) Field of Search .............................. 514/318; 546/194

(56) References Cited

U.S. PATENT DOCUMENTS 5,792,778    8/1998   de Laszlo et al. ................... 546/194

FOREIGN PATENT DOCUMENTS

WO 97/16426    5/1997   (WO).
WO 97/48725   12/1997   (WO).

OTHER PUBLICATIONS

Lowenthal, et al., Database Medline on Stn. No. 97474409, Abstract. J. Interferon and Cytokine Res., vol. 17 (9), pp. 551–558, 1997.

*Primary Examiner*—Zinna Northington Davis
(74) *Attorney, Agent, or Firm*—Mollie M. Yang; David L. Rose

(57) ABSTRACT

Trisubstituted pyrroles are antiprotozoal agents useful in the treatment and prevention of protozoal diseases in human and animals, including the control of coccidiosis in poultry.

17 Claims, No Drawings

DIARYL PIPERIDYL PYRROLE DERIVATIVES AS ANTIPROTOZOAL AGENTS

CROSS-REFERENCE TO RELATED APPLICATIONS

This application is a non-provisional application related to U.S. Provisional Application Ser. No. 60/165,142 filed on Nov. 12, 1999 priority of which is claimed hereunder.

BACKGROUND OF THE INVENTION

Parasitic protozoa are responsible for a wide variety of infections in man and animals. Many of the diseases are life threatening to the host and cause considerable economic loss in animal husbandry. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in Africa and South America; and opportunistic infections in immunocompromised hosts caused by *Pneumocystis carinii, Toxoplasma gondii*, Cryptosporidium sp. are becoming increasingly significant in the developed countries.

A protozoal infection of great economic importance is coccidiosis, a widespread disease of domesticated animals produced by infections by protozoa of the genus Eimeria. Some of the most significant of Eimeria species are those in poultry namely *E. tenella, E. acervulina, E. necatrix, E. brunetti* and *E. maxima*. The disease is responsible for high levels of morbidity and mortality in poultry and can result in extreme economic losses.

In some protozoal diseases, such as Chagas disease, there is no satisfactory treatment; in others, drug-resistant strains of the protozoa may develop. Accordingly, there exists a continued need to identify new and effective anti-protozoal drugs.

U.S. Pat. No. 5,792,778 discloses compounds of the formula:

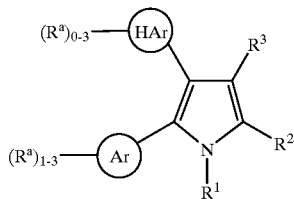

in which HAr may be 4-pyridyl, Ar may be 4-fluorophenyl, $R^2$ may be substituted 4-piperidyl and $R^3$ may be hydrogen.

SUMMARY OF THE INVENTION

The instant invention is concerned with diarylpyrrole derivatives which are useful as antiprotozoal agents. Thus, it is an object of this invention to describe such compounds. It is a further object to describe processes for the preparation of such compounds. Another object is to describe methods and compositions which use the compounds as the active ingredient thereof. Further objects will become apparent from reading the following description.

DETAILED DESCRIPTION OF THE INVENTION

The present invention provides compounds of formula I:

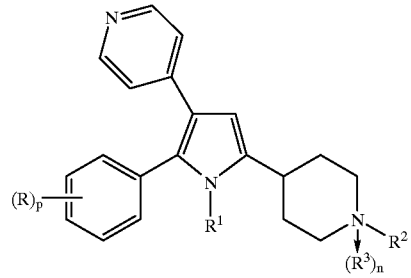

I or a physiologically acceptable salt thereof, n is 0 or 1;
m is 0, 1 or 2;
p is 1 or 2 or 3;
R is halogen;
$R^1$ is (1) hydrogen or
(2) $C_{1-6}$ alkyl;
$R^2$ is (1) $C_{3-12}$alkyl optionally substituted with 1 to 5 groups selected from $R^a$,
(2) $C_{1-2}$alkyl substituted with 1 to 3 groups selected from $R^a$,
(3) $C_{2-12}$alkenyl optionally substituted with 1 to 5 groups selected from $R^a$,
(4) $C_{2-12}$alkynyl optionally substituted with 1 to 5 groups selected from $R^a$,
(5) $C_{3-7}$cycloalkyl-$(C_{1-6}$alkyl$)_n$, optionally substituted with 1 to 5 groups selected from $R^a$ and $C_{1-6}$alkyl,
(6) aryl-$(C_{1-6}$alkyl$)_n$ wherein aryl is optionally substituted with 1 to 5 groups selected from Rb,
(7) heteroaryl-$(C_{1-6}$alkyl$)_n$ wherein heteroaryl is optionally substituted with 1 to 5 groups selected from $R^b$,
$R^3$ is (1) O or
(2) $CH_3$;
$R^a$ is (1) halogen,
(2) $N_3$,
(3) CN,
(4) $NO_2$, or
(5) $P(O)(OR^c)_2$;
$R^b$ is (1) a group selected from $R^a$,
(2) $C_{1-6}$alkyl optionally substituted with 1 to 6 groups selected from $R^a$, $OR^c$, $OCOR^c$, $NR^cR^c$, $NHCOR^c$, $NHSO_2R^c$,
(3) aryl optionally substituted with 1 to 3 groups selected from $R^a$, $OR^c$, $OCOR^c$; $NR^cR^c$, $NHCOR^c$, $NHSO_2R^c$,
(4) heteroaryl optionally substituted with 1 to 3 groups selected from $R^a$, $OR^c$, $OCOR^c$, $NR^cR^c$, $NHCOR^c$, $NHSO_2R^c$,
(5) $C(O)OR^c$,
(6) $C(O)R^c$,
(7) $S(O)_mR^c$,
(8) $OR^c$,
(9) $OC(O)NR^cR^c$,
(10) $OC(O)OR^c$,
(11) $OC(O)R^c$,
(12) $OSO_2R^c$,
(13) $NR^cR^c$,
(14) $NR^dSO_2R^c$,
(15) $NR^dC(O)OR^c$,
(16) $NR^dC(O)R^c$,
(17) $NR^dC(O)NR^cR^c$;
$R^c$ is (1) hydrogen,
(2) $C_{1-2}$alkyl optionally substituted with 1 to 5 groups selected from halogen, CN, OH and $C_{1-10}$alkoxy optionally substituted with oxiranyl, hydroxy or $C_{1-6}$ alkyl,
(3) $C_{2-12}$alkenyl,
(4) $C_{2-12}$alkynyl,
(5) $C_{3-7}$cycloalkyl-$(C_{1-6}$alkyl$)_n$, -continued (6) aryl($C_{1-6}$alkyl)$_n$ optionally substituted with $NO_2$, $C_{1-6}$alkyl, $C_{1-6}$alkoxy, or halogen,
(7) heteroaryl($C_{1-6}$alkyl)$_n$, or two $R^c$ groups together with the nitrogen atom to which they are attached form a 3- to 7-membered ring optionally containing an additional heteroatom selected from O, S and N-$R^d$;

$R^d$ is      (1) hydrogen or
           (2) $C_{1-6}$alkyl.

with the proviso that the following compounds are excluded: 2-(4-fluorophenyl)-5-(1-benzyl-4-piperidinyl)-3-(4-pyridinyl)pyrrole and 2-(4-fluorophenyl)-5-(1-phenyl-4-piperidinyl)-3-(4-pyridinyl)pyrrole.

In one subset of formula I $R^2$ is $C_{3-12}$alkyl. Preferably $R^2$ is $C_{2-6}$alkyl, and more preferably ethyl.

In another subset of formula I $R^2$ is $C_{3-6}$cycloalkyl or $C_{3-6}$cycloalkyl-$C_{1-3}$alkyl wherein said cycloalkyl is optionally substituted with 1 or 2 groups selected from $R^a$ and $C_{1-3}$alkyl.

In another subset of formula I, $R^2$ is aryl-$C_{1-3}$alkyl wherein said aryl is substituted with 1 to 3 groups selected from $R^b$.

In another subset of formula I, $R^2$ is heteroaryl-$C_{1-3}$alkyl wherein said heteroaryl is optionally substituted with 1 to 3 groups selected from $R^b$.

Compounds of formula Ia represent one embodiment of formula I:

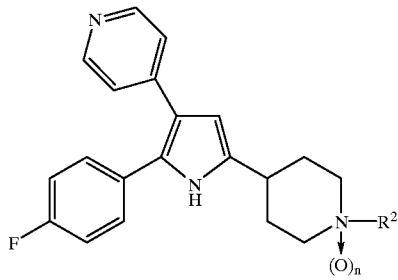

Ia wherein $R^2$ is $C_{3-12}$alkyl, $C_{3-6}$cycloalkyl or $C_{3-6}$cycloalkyl-$C_{1-3}$alkyl wherein said cycloalkyl is optionally substituted with 1 or 2 groups selected from $R^a$ and $C_{1-3}$alkyl, aryl-$C_{1-3}$alkyl wherein said aryl is substituted with 1 to 3 groups selected from $R^b$, heteroaryl-$C_{1-3}$alkyl wherein said heteroaryl is optionally substituted with 1 to 3 groups selected from $R^b$.

In one subset of formula Ia, $R^2$ is $C_{3-6}$alkyl. Examples of $C_{3-6}$alkyl include n-propyl, isopropyl, n-butyl, isobutyl, sec-butyl, 2-pentyl, 3,3-dimethylbutyl, 2-hexyl, 4-methyl-2-pentyl, 2-ethylbutyl, 2-methylbutyl, and 2-methylpentyl.

In another subset of formula Ia, $R^2$ is $C_{3-6}$cycloalkyl or $C_{3-6}$cycloalkyl-$C_{1-3}$alkyl wherein said cycloalkyl is optionally substituted with 1 or 2 groups selected from $C_{1-3}$alkyl; examples include cyclopropylmethyl, cyclobutyl, cyclobutylmethyl, cyclopentyl, 2-methylcyclopentyl and cyclohexyl.

In another subset of formula Ia, $R^2$ is substituted benzyl in which the substituents are one or two groups selected from halogen, $OR^c$, $OC(O)R^c$, $OC(O)NR^cR^c$, $OC(O)OR^c$, $C_{1-3}$alkyl optionally substituted with $OR^c$, $NR^cR^c$, and cyano. Examples of substituted benzyl include 2-hydroxybenzyl, 3-hydroxybenzyl, 4-hydroxybenzyl, 4-methoxybenzyl, 2-chloro-4-hydroxybenzyl, 2,4-dihydroxybenzyl, 4-(N-phenylcarbamoyloxy)benzyl, 4-hydroxy-2-methoxybenzyl, 4-acetoxybenzyl, 4-(propanoyloxy)benzyl, 4-(2-hydroxyethyl)benzyl, 4-(3-(N,N-dimethylamino)propyl)-benzyl, 3-ethoxy-4-methoxybenzyl, 3-ethoxy-4-hydroxybenzyl, 2-methylbenzyl, 2-cyanobenzyl, 2-trifluoromethylbenzyl, 4-trifluoromethylbenzyl, 4-trifluoromethoxy-benzyl, 2-difluoromethoxybenzyl, 3-bromo-4-fluorobenzyl, 4-methylbenzyl, 4-nitro-benzyl, 4-chlorobenzyl, 2,4-dichlorobenzyl, 3,4-dichlorobenzyl and 3,4-difluoro-benzyl.

In another subset of formula Ia, $R^2$ is heteroaryl-methyl wherein said heteroaryl is optionally substituted with 1 or 2 groups selected from $S(O)_mR^c$, $C_{1-6}$alkyl optionally substituted with hydroxy, and halogen. Examples of heteroaryl portion of the heteroaryl include 5-(methylthio)-2-thienyl, 2-pyridyl, 3-pyridyl, 4-pyridyl, 4-quinolinyl, 2-quinolinyl, 6-methyl-2-pyridyl, 2-methyl-4-thiazolyl, 5-t-butyl-1,2,4-oxadiazol-3-yl, 2-pyrimidinyl, 2-thiazolyl, 5-methyl-2-thienyl, 2-imidazolyl, 1-methyl-2-pyrrolyl, 2-furyl, 4-methyl-5-imidazolyl, 3-thienyl, 5-methyl-2-furyl, 5-(hydroxymethyl)-2-furyl, 3-methyl-2-thienyl, 3-methyl-2-pyrrolyl, 2-thiazolyl, 5-ethyl-2-thiazolyl, 2-methyl-3-pyridyl and 4-imidazolyl.

As used herein, unless otherwise defined or limited, the following definitions apply:

"Alkyl" includes straight or branched carbon chains of the designated length. Exemplary of such alkyl groups are methyl, ethyl, propyl, isopropyl, butyl, sec-butyl, tertiary butyl, pentyl, isopentyl, hexyl, isohexyl, and the like.

"Alkenyl" includes straight and branched carbon chains of the designated length having at least one carbon-carbon double bond. Examples of alkenyl group include vinyl, allyl, 1-propenyl, 2-propenyl, isobutylenyl, hexenyl, hexadienyl, octenyl, and the like.

"Alkynyl" includes straight and branched carbon chains of the designated length having at least one carbon-carbon triple bond. Examples of alkynyl group include ethynyl, propargyl, 1-butynyl, 2-butynyl, 3-butynyl, 4-pentynyl, and the like.

The term "cycloalkyl" is a saturated carbocyclic ring with the designated number of ring carbon atoms.

The term "halogen" is intended to include the halogen atoms fluorine, chlorine, bromine and iodine.

The term "aryl" is an aromatic mono- or bicyclic carbocycle having from 6 to 10 carbon atoms, optionally fused to a 4- to 6-membered non-aromatic ring containing 0–3 heteroatoms selected from N, O and S(O) m. Examples include phenyl methylenedioxyphenyl and naphthyl.

"Heteroaryl" is a mono-or bicyclic aromatic ring containing from 1 to 6 heteroatoms independently selected from N, O and S(O)m wherein each ring has five or six ring atoms. Examples of heteroaryl include pyridyl, pyrimidinyl, pyrrolyl, furyl, thienyl, imidazolyl, thiazolyl, thiadiazolyl, triazolyl, tetrazolyl, oxadiazolyl, oxazolyl, imidazolidinyl, pyrazolyl, isoxazolyl, benzothiadiazolyl, indolyl, indolinyl, benzodioxolyl, benzodioxanyl, benzothiophenyl, benzofuranyl, benzimidazolyl, benzisoxazolyl, benzothiazolyl, quinolinyl, benzotriazolyl, benzoxazolyl, purinyl, furopyridine and thienopyridine.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I as individual isomers as well as mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed within compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of the general Formula I may be obtained by stereospecific synthesis using optically pure starting materials or reagents of known configuration.

The term "physiologically acceptable salts" refers to salts prepared from non-toxic bases or acids that are physiologically acceptable to the host. When the compound of the present invention is acidic, salts may be prepared from physiologically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. In one embodiment the salts are selected from ammonium, calcium, magnesium, potassium and sodium salts. Salts derived from physiologically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from physiologically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. In one embodiment acids are selected from citric, hydrobromic, hydrochloric, maleic, phosphoric, sulfuric, and tartaric acids.

Compounds of the present invention may be prepared using a variety of organic synthesis methodologies well known in the art. Examples of suitable procedures are described in the following schemes.

SCHEME 1

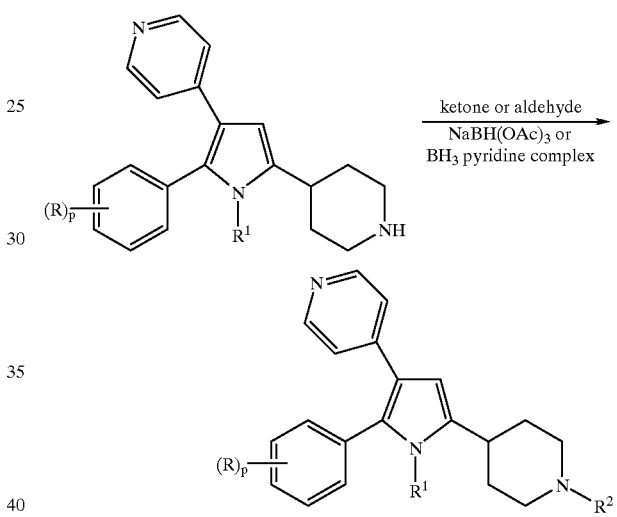

wherein $R^2$ is optionally substituted alkyl, alkenyl, alkynyl, cycloalkyl, aralkyl, (cycloalkyl)alkyl, heteroaryl or heteroaralkyl Alkylation of the piperidine nitrogen atom may be carried out by reductive amination as shown in Scheme 1. The reaction is carried out by treating the piperidine compound with a ketone or an aldehyde in the presence of BH3 pyrdine complex or sodium triacetoxyborohydride to give the desired alkylated piperidines.

SCHEME 2

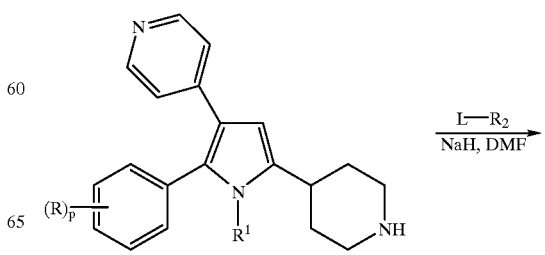

-continued

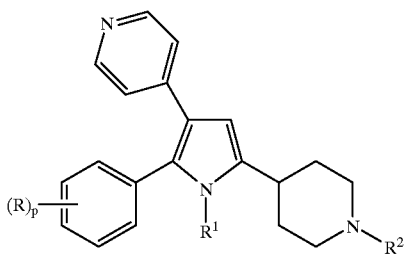

where L is a leaving group such as bromide, chloride, iodide

Scheme 2 depicts another method for the alkylation of the piperidine nitrogen atom. The piperidine compound is treated with a strong base such as sodium hydride in solvent such as DMF followed by L-R$^2$ wherein L is a leaving group to give the desired tertiary amines.

SCHEME 3

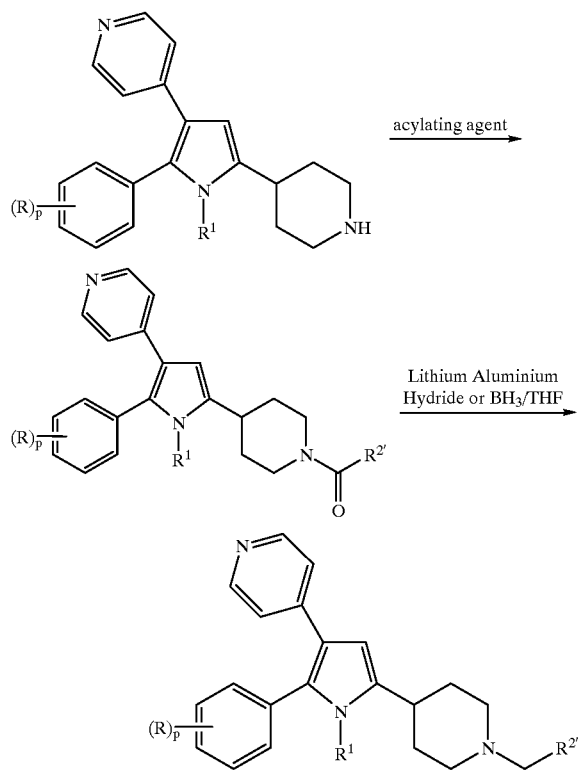

wherin R$^{2'}$ is R$^2$ less one methylene unit.

The acylation of the piperidine amine is depicted in Scheme 3. Acylation may be conveniently carried out using an acylating agent such as an acid chloride, acid anhydride, or a carboxylic acid in the presence of a coupling agent such as dicyclohexylcarbodiimide, EDC, PyBOP and the like. The resulting amide may be reduced using, for example, a borane reagent or lithium aluminum hydride and the like to provide the corresponding tertiary amine.

N-oxides are prepared by treating the amine in dichlormethane with one equivalent of m-chloroperbenzoic acid, treatment with sodium bicarbonate to remove acid and final purification of N-oxide by prep TLC on silica plate eluted with NH4OH/methanol/dichlormethane 1:9:90.

In some cases, the products from the reactions described in Schemes 1 to 3 may be further modified, for example, by the removal of protecting groups or the further elaboration of free amino or hydroxy groups. These manipulations may include, but are not limited to, reduction, oxidation, alkylation, acylation, and hydrolysis reactions, which are commonly known to those skilled in the art.

Utility

The diaryl pyrroles of the present invention are useful as antiprotozoal agents. As such, they may be used in the treatment and prevention of protozoal diseases in human and animals, including poultry. Examples of protozoal diseases against which compounds of formula I may be used, and their respective causative pathogens, include: 1) amoebiasis (Dientamoeba sp., *Entamoeba histolytica*); 2) giardiasis (*Giardia lamblia*); 3) malaria (Plasmodium species including *P. vivax, P. falciparum, P. malariae and P. ovale*); 4) leishmaniasis (Leishmania species including *L. donovani, L. tropica, L. mexicana, and L. braziliensis*); 5) trypanosomiasis and Chagas disease (Trypanosoma species including *T. brucei, T. theileri, T. rhodesiense, T. gambiense, T. evansi, T. equiperdum, T. equinum, T. congolense, T. vivax* and *T. cruzi*); 6) toxoplasmosis (*Toxoplasma gondii*); 7) babesiosis (Babesia sp.); 8) cryptosporidiosis (Cryptosporidium sp.); 9) dysentery (*Balantidium coli*); 10) vaginitis (Trichomonas species including *T. vaginitis*, and *Tritrichomonas foetus*); 11) coccidiosis (Eimeria species including *E. tenella, E. necatrix, E. acervulina, E. maxima and E. brunetti, E. mitis, E. bovis, E. melagramatis*, and Isospora sp.); 12) enterohepatitis (*Histomonas gallinarum*), and 13) infections caused by Anaplasma sp., Besnoitia sp., Leucocytozoan sp., Microsporidia sp., Sarcocystis sp., Theileria sp., and *Pneumocystis carinii*.

Dose Range

Compounds of formula I may be administered to a host in need of treatment in a manner similar to that used for other antiprotozoal agents; for example, they may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art. For the treatment of protozoal diseases in humans, the oral dosage may range from 1 mg/kg to 1000 mg/kg; and the parenteral dosage may range from 0.5 mg/kg to 500 mg/kg. For veterinary therapeutic use, the oral dosage may range from 1 mg/kg to 1000 mg/kg; and the parenteral dosage may range from 0.5 mg/kg to 500 mg/kg. For prophylactic use in humans, the oral dosage may range from 1 mg/kg to 1000 mg/kg; and the parenteral dosage may range from 0.5 mg/kg to 500 mg/kg. For prophylactic use in animal, the oral dosage may range from 1 mg/kg to 1000 mg/kg; and the parenteral dosage may range from 0.5 mg/kg to 500 mg/kg. For use as an anticoccidial agent, particularly in poultry, the compound is may be administered in the animals' feed or drinking water in accordance with common practice in the pountry industry as described below.

Composition

The compositions of the present invention comprises a compound of formula I and an inert carrier. The compositions may be in the form of pharmaceutical compositions for human and veterinary usage, or in the form of feed composition for the control of coccidiosis in poultry.

The pharmaceutical compositions of the present invention comprise a compound of formula I as an active ingredient, and may also contain a physiologically acceptable carrier and optionally other therapeutic ingredients. The compositions include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, compounds of formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, compounds of formula I may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid may be presented as unit dose suppositories. Suitable carriers include cocoa butter and other materials commonly used in the art, and the suppositories may be conveniently formed by admixture of the combination with the softened or melted carrier(s) followed by chilling and shaping molds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

For use in the management of coccidiosis in poultry, a compound of formula I may be conveniently administered as a component of a feed composition. Suitable poultry feed composition will typically contain from about 1 ppm to about 1000 ppm, or from about 0.0005% to about 0.05% percent, by weight of a compound of formula I. The optimum levels will naturally vary with the species of Eimeria involved, and can be readily determined by one skilled in the art.

In the preparation of poultry feed, a compound of formula I may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuff include molasses, fermentation residues, corn meal, ground and rolled oats, wheat shorts and middlings, alfalfa, clover and meat scraps, together with mineral supplements such as bone meal, calcium carbonate and vitamins.

When the compound according to the present invention is used as an additive to the feed, it is typically incorporated into a "premix." The premix contains the active agent or agents as well as physiologically acceptable carriers and feedstuffs. The premix is relatively concentrated and is adapted to be diluted with other carriers, vitamin and mineral supplements, and feedstuffs to form the final animal feed. Premixes which are intermediate in concentration of active agent between a first premix and the final animal feed are sometimes employed in the industry and can be used in implementing the present invention. When employing the present compound as sole active agent, a premix desirably contains the agent at a concentration of from 0.1 to 50.0% by weight. Preferred premixes will generally contain the present compound at a concentration of from 0.5 to 25.0%, by weight. The identity of the other components of the premix and ultimate animal feed is not critical. In final feeds, the concentration of the active agent is not critical and will depend on various factors known to those skilled in the art. Such factors include the relative potency of the particular active agent and the severity of the coccidial challenge. In general, a final feed employing compound of the present invention as the sole anticoccidial will contain from about 0.0005 to about 0.05% by weight of said compound, preferably from about 0.0005 to about 0.005%.

Compositions containing a compound of formula I may also be prepared in powder or liquid concentrate form. In accordance with standard veterinary formulation practice, conventional water soluble excipients, such as lactose or sucrose, may be incorporated in the powders to improve their physical properties. Thus one embodiment of suitable powders of this invention comprises 50 to 100% w/w, and for example 60 to 80% w/w of the compound and 0 to 50% w/w and for example 20 to 40% w/w of conventional veterinary excipients. These powders may either be added to animal feedstuff, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The present invention contemplates using a compound of formula (1) as sole anticoccidial agent as well as in combination with one or more other anticoccidial agents. Suitable anticoccidials for combination use include, but are not limited to, amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril. When used in combination with one or more other anticoccidial agent, the compound of formula (I) may be administered at or lower than the effective doses when used alone; for example, the final feed may contain about 0.0001 to about 0.02% by weight, or preferably from about 0.0005 to about 0.005% of a compound of formula (I). Similarly, the second anticoccidial agent in the combination may be used in an amount at or lower than those commonly used as a sole anticoccidial. The combination may be formulated into medicament for poultry use as described previously.

The formulated medicament may contain, in addition to anticoccidial agent(s) other therapeutic or nutritional agents commonly administered to poultry in the feed or drinking water; such other agents may be, for example, parasiticides, antibacterials, and growth promoters.

Anticoccidiosis Assay.

One-day-old White Leghorn chickens are obtained from a commercial hatchery and acclimated in a holding room. At three days of age the test animals are selected by weight, wingbanded, and randomly placed on medicated or control diets for the duration of the experiment. One or two replicates of two birds are utilized per treatment. Following 24 h premedication, in each replicate one bird is infected with Eimeria acervulina, the other bird is infected with E. tenella.

Both strains of Eimeria are sensitive to all anticoccidial products, and have been maintained in laboratory conditions for over 25 years. The inocula consist of sporulated oocysts in tap water suspensions, administered at a dose rate of 0.25 ml per bird. The inocula levels are selected by previous dose titrations to provide a low to moderate level of infection. The E. acervulina portion of the experiment is terminated on Day 5, the E. tenella on Day 6 post infection. The measured parameters are weight gain, feed consumption and oocyst production. E. tenella lesion scores are also recorded for background information. Treatments which provide at least 80% reduction in oocyst production are considered active, those with 50–79% are considered partially active, and those with <50% are considered inactive. The same numerical categories in weight gain and feed consumption differentiate among treatments with good, fair or poor productivity.

REFERENCE EXAMPLE 2-(4-fluorophenyl)-5-(piperidin-4-yl)-3-(4-pyridinyl)-pyrrole

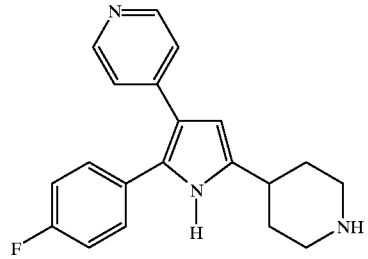

Step 1. 1-(4-fluorophenyl)-2-(4-pyridinyl)-ethanone

To a solution of lithium diisopropyl amide (2.0 M in heptane, tetrahydrofuran, ethyl benzene) 3.1 mL (6.3 mmol) in 6 mL of anhydrous tetrahydrofuran at −78° C. under nitrogen was added 0.5 g (5.3 mmol) of 4-picoline dropwise. The reaction mixture was stirred for 20 minutes and then treated with a solution of 0.9 g (5.3 mmol) of 4-fluoro-(N-methyl-N-methoxy)-benzamide in tetrahydrofuran. The reaction mixture was warmed to 0° C. and quenched by addition of 10 mL of brine. The mixture was extracted with ethyl acetate (3×10 mL) and the combined organic phases were dried over $MgSO_4$. The mixture was filtered and the filtrate was concentrated in vacuo to give the title compound as an orange solid. H$I$NMR (CDCl$_3$300 MHz): 4.23 s (d, 2H), 7.1–7.18 m (4H), 8.02 (dd, 2H), 8.55 (dd, 2H).

Step 2. 4-(1-benzyloxycarbonylpiperidin-4-yl)-2-(4-pyridyl)-1-(4-fluoro-phenyl)butane-1,4-dione To a solution of the product of Step 1 (0.5 g (2.3 mmol)) in 5.0 ml of dry dimethyl sulfoxide was added 2.4 ml (2.4 mmol) of a 1M solution of sodium hexamethyldisilazide in tetrahydrofuran. After 10 minutes, a solution of 0.72 g (2.4 mmol) of the product of 4-(2-iodoacetyl)-1-(benzyloxycarbonyl)piperidine was added in 1 ml dimethyl sulfoxide dropwise. The reaction mixture was stirred for 2 hours, diluted with ethyl acetate (EtOAc, 20 ml) and washed with water (3×10 ml). The combined organic phases were washed with brine and dried over $MgSO_4$. The mixture was filtered and the filtrate was concentrated in vacuo. The residue was purified by MPLC over silica gel eluting with 2% MeOH/$CH_2Cl_2$ to give the desired product. FAB ms: C28H27N2O4F:474; Observed: 475 ($M^+$+1).

Step 3. 2-(4-fluorophenyl)-5-(1-benzyloxycarbonylpiperidin-4-yl)-3-(4-pyridinyl)pyrrole The product of Step 2 was heated in 5 ml of acetic acid in the presence of 2.0 g ammonium acetate at 110° C. for 1.5 hours. The reaction mixture was diluted with EtOAc (10 mL) and washed with water. The combined organic phases were washed with brine and dried over MgSO$_4$. The mixture was filtered and the filtrate was concentrated in vacuo. The residue was purified by MPLC over silica gel eluting with 2% MeOH/CH$_2$Cl$_2$ to give the desired product. H$^1$-NMR (CDCl$_3$, 300 MHz): 1.67 (m, 2H); 2.02 (bd, 2h); 2.75–3.0 (m, 3H); 4.29 bd, 2H); 5.12 (s, 2H); 6.19 (d, 1H); 7.03 (t, 2H); 7.18 (dd, 2H); 7.25–7.39 (m, 6H); 8.39 (dd, 2H); 8.52 (bs, 1H). FAB ms: C28H26N3O2F:455; Observed: 456 (M$^+$+1).

Step 4. 2-(4-fluorophenyl)-5-(piperidin-4-yl)-3-(4-pyridinyl)pyrrole acetate salt The product of Step 3 (183 mg) was dissolved in 5 ml of acetic acid. The solution was hydrogenated over 25 hours at atmospheric pressure in the presence of 10 mg of 10% Pd/C. The mixture was filtered and the filtrate was concentrated in vacuo to give the product. FAB ms: C$_{20}$H$_{20}$N$_3$F:321; Observed: 322 (M$^+$+1).

The following examples are provided to more fully illustrate the invention and are not to be construed as limiting the scope of the invention in any manner. In the general procedures, reaction conditions such as temperature, time, solvent may be varied depending on the reagents used, products to be made, etc. The selection of such variables are within the skills of a person having ordinary skill in the art.

Compounds exemplified below are of the general formula

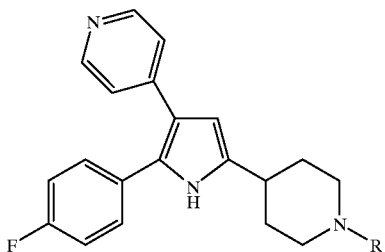

In the examples only the N—R portion is depicted. The term BOC stands for t-butyloxycarbonyl, Ph stands for phenyl and Ac stands for acetyl.

NMR data are collected on a Varian XL400 spectrometer. Compounds were dissolved in CDCl$_3$ or CDCl$_3$ containing 1–2 drops of CD$_3$OD, unless otherwise specified.

General Procedure for Reductive Amination Using Borane

The compound of Reference Example and the appropriate carbonyl compound are dissolved in ethanol. Borane-pyridine complex is added and the reaction mixture is stirred at room temperature to about 60° C., under nitrogen atmosphere overnight. The reaction mixture is concentrated, and purified by preparative TLC eluting with 5% MeOH (10% NH$_3$.H$_2$O)/CH$_2$Cl$_2$ to give the desired product.

The following compounds were prepared in accordance with the above-described procedure:

| Ex. | N-R | carbonyl | NMR |
|---|---|---|---|
| 1 | (N-CH$_2$-2-hydroxyphenyl) | 2-hydroxybenzaldehyde | 1.8 (m, 2H), 2.0 (m, 2H), 2.3 (m, 2H), 2.6 (m, 1H), 3.1 (m, 2H), 3.7 (s, 2H), 6.1 (s, 1H), 6.7 (m, 2H), 6.9 (m, 3H), 7.1 (m, 4H), 7.2 (m, 3H), 8.2 (broad, 2H). |
| 2 | (N-CH$_2$-2-chloro-4-hydroxyphenyl) | 2-chloro-4-hydroxybenzaldehyde | 1.8 (m, 4H), 2.2 (m, 2H), 2.6 (m, 1H), 3.0 (m, 2H), 3.6 (s, 2H), 6.1 (s, 1H), 6.7 (m, 1H), 6.8 (m, 1H), 7.0 (m, 2H), 7.2 (m, 6H), 8.3 (m, 2H). |
| 3 | (N-CH$_2$-4-OBOC-phenyl) | 4-BOC-benzaldehyde | 1.6 (s, 9H), 1.8 (m 2H), 2.0 (m, 2H), 2.1 (m, 2H), 2.6 (m, 1H), 3.0 (m, 2H), 3.6 (s, 2H), 6.2 (s, 2H), 7.0 (m, 2H), 7.1 (m, 2H), 7.2 (m, 2H), 7.3 (m, 4H), 8.2 (broad, 1H), 8.4 (m, 2H). |
| 4 | (N-CH$_2$-2,4-dihydroxyphenyl) | 2,4-dihydroxybenzaldehyde | 1.8 (broad, 2H), 2.0. (m, 2H), 2.2 (m, 2H), 2.7 (m, 1H), 3.2 (m, 2H), 3.7 (s, 2H), 6.1 (s, 1H), 7.0 (m, 2H), 7.1 (m, 2H), 7.3 (m, 2H), 8.3 (m, 2H). |
| 5 | (N-2-methylcyclopentyl) | 2-methylcyclopentanone | 1.0–3.4 (broad, 20H), 6.1 (s, 1H), 7.0 (m, 2H), 7.2 (m, 2H), 7.3 (m, 2H), 8.3 (m, 2H). |

-continued

| Ex. | N-R | carbonyl | NMR |
|---|---|---|---|
| 6 | 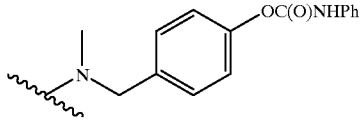 | 4-(N-phenyl-carbamoyloxy)-benzaldehyde | 1.8 (m, 2H), 2.0 (m, 2H), 2.8 (m, 1H), 3.0 (m, 2H), 4.2 (m, 2H), 6.2 (s, 1H), 6.5 (s, 1H), 7.0 (m, 2H), 7.2 (m, 2H), 7.3 (m, 7H), 8.4 (m, 2H), 8.6 (broad, 1H) |
| 7 | 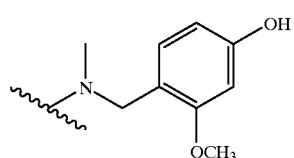 | 2-methoxy-4-hydroxybenz-aldehyde | 1.8 (m, 4H), 2.2 (m, 1H), 2.6 (m, 2H), 3.0 (m, 2H), 3.6 (broad, 2H), 3.9 (s, 3H), 6.0 (s, 1H), 6.4 (m, 2H), 7.0 (m, 3H), 7.2 (m, 2H), 7.3 (m, 2H), 8.2 (m, 2H) |
| 8 | 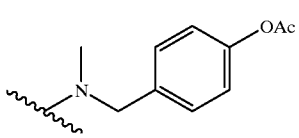 | 4-acetoxybenz-aldehyde | 1.8 (m, 2H), 2.0 (m, 2H), 2.1 (m, 2H), 2.3 (s, 3H), 2.6 (m, 1H), 3.0 (m, 2H), 3.6 (s, 2H), 6.2 (s, 1H), 7.0 (m, 4H), 7.2 (m, 2H), 7.3 (m, 2H), 7.4 (m, 2H), 8.2 (broad, 1H), 8.4 (m, 2H) |
| 9 | 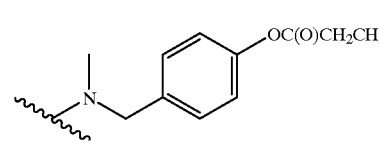 | 4-propioxybenz-aldehyde | 1.3 (m, 3H), 1.8 (m, 2H), 2.0 (m, 2H), 2.1 (m, 2H), 2.3 (s, 3H), 2.6 (m, 3H), 3.0 (m, 2H), 3.6 (s, 2H), 6.2 (s, 1H), 7.0 (m, 4H), 7.2 (m, 2H), 7.3 (m, 2H), 7.4 (m, 2H), 8.2 (broad, 1H), 8.4 (m, 2H) |
| 10 | 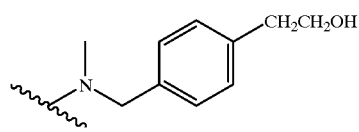 | 4-[(2-hydroxy)-ethyl]benz-aldehyde | 1.8 (m, 2H), 2.0 (m, 2H), 2.1 (m, 2H), 2.6 (m, 1H), 3.0 (m, 2H), 3.5 (s, 2H), 3.9 (m, 2H), 4.1 (m, 2H), 6.2 (d, J = 0.9 Hz, 1H), 6.8 (m, 2H), 7.0 (m, 2H), 7.2 (m, 2H), 7.3 (m, 4H), 8.4 (m, 2H), 8.6 (broad, 1H) |
| 11 | 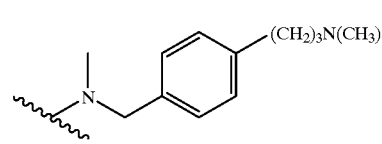 | 4-[3-(N,N-dimethylamino)-propyl]benz-aldehyde | 1.8 (m, 2H), 2.0 (m, 4H), 2.1 (m, 2H), 2.4 (t, J = 7.0 Hz, 2H), 2.6 (m, 1H), 3.0 (m, 2H), 3.5 (s, 2H), 4.0 (t, J = 6.5 Hz, 2H), 6.2 (s, 1H), 6.8 (m, 2H), 7.0 (m, 2H), 7.2 (m, 6H), 8.4 (m, 2H), 8.5 (broad, 1H) |
| 12 | 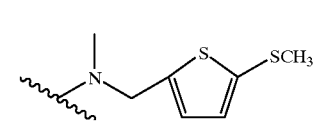 | 5-(methylthio)-2-thiophenecarbox-aldehyde | 2.46(s, 3H), 3.69(s, 2H), 6.75(b, J = 3.6 Hz, 1H), 6.90(d, J = 3.6 Hz, 1H). |
| 13 | 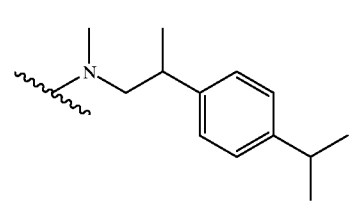 | 2-[(4-isopropyl)-phenyl]propion-aldehyde | 1.24(m, 9H), 2.02(m, 1H), 2.86(m, 1H) 2.96(m, 2H), 7.10(m, 4H). |
| 14 | 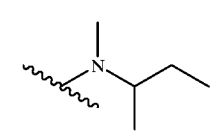 | 2-butanone | 0.92(t, J = 7.4 Hz, 3H), 1.05(d, J = 5.5 Hz, 3H), 1.34(m, 2H), 2.64(m, 1H). |

| Ex. | N-R | carbonyl | NMR |
|---|---|---|---|
| 15 | N-methyl-N-(pentan-2-yl) | 2-hexanone | 0.88(t, J = 6.6 Hz, 3H), 1.03(d, J = 6.4 Hz, 3H), 1.29(m, 4H), 2.65(m, 1H). |
| 16 | N-methyl-N-(3-phenylbutyl) | 3-phenylbutyr-aldehyde | 1.25(d J = 7.0 Hz, 3H), 1.70(m, 2H), 2.00(m, 2H), 2.74(m, 1H), 7.24(m, 5H). |
| 17 | N-methyl-N-(5-methylhexan-2-yl) | 5-methyl-2-hexanone | 0.87(m, 6H), 1.05(d, J = 6.5Hz, 3H), 1.20(m, 1H), 1.58(m, 2H), 1.89(m, 2H), 2.46(m, 1H). |
| 18 | N-methyl-N-[3-(4-hydroxyphenyl)butyl] | 4-(4-hydroxyphenyl)-2-butanone | 1.04(d, J = 6.5 Hz, 3H), 1.7(m, 2H), 2.62(m, 3H). |
| 19 | N-methyl-N-(4-methylpentan-2-yl) | 4-methyl-2-pentanone | 0.91(m, 6H), 1.10(d, J = 6.2 Hz, 3H), 1.23(m, 1H), 1.68(m, 2H), 2.84(m, 1H). |
| 20 | N-methyl-N-(1,3-benzodioxol-5-ylmethyl) | Piperonal | 9.07(s, br, 1H), 8.36(d, J = 4.76 Hz, 2H), 7.40~7.20(m, 7H), 7.16(d, J = 5.86 Hz, 2H), 7.00(m, 2H), 6.14(s, 1H), 3.63(s, 2H), 3.18(m, 1H), 3.05(m, 2H), 2.86(m, 1H), 2.72(m, 1H), 2.63(m, 2H), 2.52(m, 1H), 2.21(m, 2H), 2.10~1.93(m, 5H), 1.87(m, 1H); MS(M + 1) = 456.2 |
| 21 | N-methyl-N-(pyridin-2-ylmethyl) | 2-pyridinecarbox-aldehyde | 8.57(m, 1H), 7.68(m, 1H), 7.19(m, 1H), 3.77(s, 2H); MS(M + 1) = 413.3 |
| 22 | N-methyl-N-(pyridin-3-ylmethyl) | 3-pyridinecarbox-aldehyde | 8.48(m, 2H), 7.67(m, 1H), 7.25(m, 1H), 3.52(s, 2H); MS(M + 1) = 413.3 |
| 23 | N-methyl-N-(pyridin-4-ylmethyl N-oxide) | 4-pyridinecarbox-aldehyde | 8.12(d, J = 6.95 Hz, 2H), 7.27(m, 2H), 3.48(s, 2H); MS(M + 1) = 429.3 |
| 24 | N-methyl-N-(1,3-benzodioxol-4-ylmethyl) | 2,3-(methylenedioxy)-benz-aldehyde | 6.80(m, 3H), 5.94(s, 2H), 3.55(s, 2H); MS(M + 1) = 456.3 |

-continued

| Ex. | N-R | carbonyl | NMR |
|---|---|---|---|
| 25 | 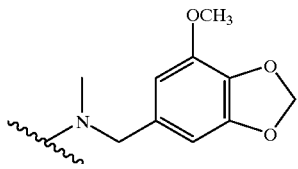 | 5-methoxy-piperonal | 6.53(s, 1H), 6.50(s, 1H), 5.94(s, 2H), 3.89(s, 3H), 3.42(s, 2H); MS(M + 1) = 486.3 |
| 26 | 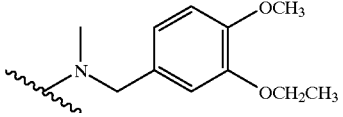 | 3-ethoxy-4-methoxybenz-aldehyde | 6.88(S, 1H), 6.82(s, 1H), 6.81(s, 1H), 4.10(q, J = 7.16 Hz, 2H), 3.84(S, 3H), 3.45(S, 2H), 1.45(t, J = 7.08 Hz, 3H); MS(M + 1) = 486.4 |
| 27 | 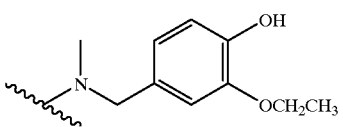 | 3-ethoxy-4-hydroxybenz-aldehyde | 6.86(m, 2H), 6.75(m, 1H), 4.11(q, J = 6.96 Hz, 2H), 3.44(s, 2H), 1.42(t, J = 6.96 Hz, 3H); MS(M + 1) = 472.4 |
| 28 | 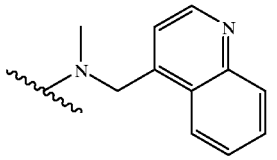 | 4-quinoline-carboxaldehyde | 8.86(d, J = 4.35 Hz, 1H), 8.24(d, 7.69, 1H), 8.11(d, J = 8.42 Hz, 1H), 7.71(t, J = 8.26 Hz, 1H), 7.56(t, J = 8.30 Hz, 1H), 7.47(d, J = 4.39 Hz, 1H), 3.99(s, 2H); MS(M + 1) = 463.4 |
| 29 | 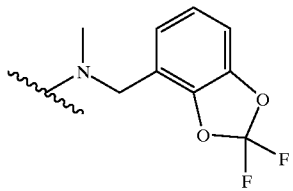 | 2,2-difluoro-4-formylbenzo-dioxole | 7.16(m, 1H), 7.00(m, 2H), 3.69(s, 2H); MS(M + 1) = 492.4 |
| 30 | 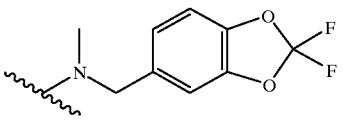 | 2,2-difluoro-5-formylbenzodioxole | 7.11(s, 1H), 7.00(m, 2H), 3.49(s, 2H); MS(M + 1) = 492.4 |
| 31 | 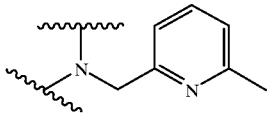 | 6-methyl-2-pyridinecarbox-aldehyde | 7.55(t, 7.69 Hz, 1H), 7.29(m, 1H), 7.15(m, 1H), 3.70(s, 2H), 2.53(s, 3H); MS(M + 1) = 427.3 |
| 32 | 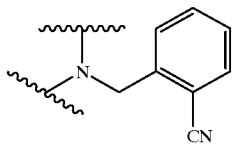 | 2-cyanobenz-aldehyde | 7.78(d, J = 5.86 Hz, 1H), 7.60(m, 1H), 7.45(m, 1H), 7.18(m, 1H), 3.47(s, 2H), MS(M + 1) = 453.4 |
| 33 | 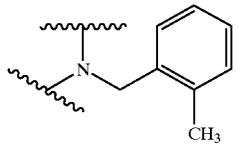 | 2-methylbenz-aldehyde | 7.29(m, 1H), 7.15(m, 2H), 3.47(s, 2H), 2.36(s, 3H), MS(M + 1) = 426.4 |

| Ex. | N-R | carbonyl | NMR |
|---|---|---|---|
| 34 | 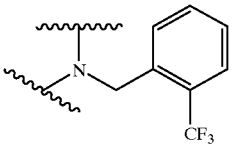 | 2-(trifluoro-methyl)benzaldehyde | 7.89(d, J = 7.60 Hz, 1H), 7.62(d, J = 7.90 Hz, 1H), 7.53(t, J = 7.12 Hz, 1H), 7.34(t, J = 7.71 Hz, 1H), 3.74(s, 2H); MS(M + 1) = 480.4 |
| 35 | 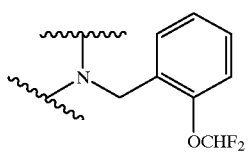 | 2-(difluoromethoxy)benzaldehyde | 7.45(d, J = 6.51 Hz, 1H), 7.28(m, overlapping, 1H), 7.21(m, 1H), 6.61(t, J = 75.1 Hz, 1H), 3.62(s, 2H); MS(M + 1) = 478.4 |
| 36 | 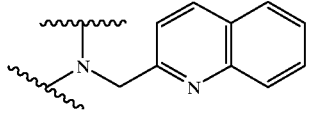 | 2-quinoline-carboxaldehyde | 8.13(d, J = 8.66 Hz, 1H), 8.06(d, J = 8.58 Hz, 1H), 7.80(d, J = 7.24 Hz, 1H), 7.67(m, 2H), 7.51(t, J = 6.92 Hz, 1H), 3.89(s, 2H); MS(M + 1) = 463.4 |

General Procedure for N-Alkylation

To a solution of the piperidine prepared in Reference example in anhydrous N,N-dimethylformamide under nitrogen at room temperature, sodium hydride is added. The solution is stirred at room temperature for 0.5 hour and the appropriate alkyl halide is added. The resulting solution is allowed to stir at room temperature overnight. The crude product is quenched by water and extracted with ethyl acetate. The organic phase is concentrated and purified by flash column silica gel chromatography to yield the desired product.

The following compounds were prepared in accordance with the above-described general procedure:

| Ex. | N—R | Alkyl Halide | NMR |
|---|---|---|---|
| 37 | 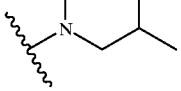 | 1-iodo-2-methyl-propane | (CD$_3$OD)2.00(m, 2H), 0.98(d, J=6.64Hz, 6H), 0.90(m, 1H) |
| 38 | 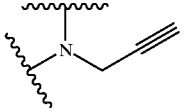 | propargyl bromide | (CD$_3$OD)3.35(d, J=2.49Hz, 2H), 2.73(m, 1H) |
| 39 | 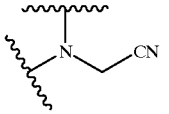 | Iodoacetonitrile | (CD$_3$OD)3.69(s, 2H) |
| 40 | 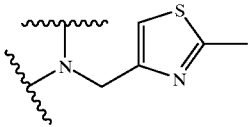 | 4-chloromethyl-2-methylthiazole.HCl | 6.95(s, 1H), 3.63(s, 2H), 2.69(s, 3H) |
| 41 | 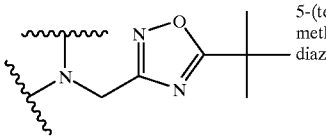 | 5-(tert-butyl)-3-chloromethyl-1,2,4-oxadiazole | 3.70(s, 2H), 1.43(s, 9H) |

-continued

| Ex. | N—R | Alkyl Halide | NMR |
|---|---|---|---|
| 42 | N-CH₂CH₂CH₂F | 1-bromo-3-fluoro-propane | 4.57(m, 2H), 4.46(m, 2H), 2.00(m, 2H) |
| 43 | N-(2-pyrimidinyl) | 2-chloropyrimidine | 8.30(d, J=4.68Hz, 2H), 6.47(t, J=4.72Hz, 1H) |
| 44 | N-(2-thiazolyl) | 2-bromothiazole | 7.17(d, J=3.66Hz, 1H), 6.56(d, J=3.67Hz, 1H) |
| 45 | N-CH₂-(4-fluorophenyl) | 4-fluorobenzyl chloride | 7.26(m, 2H), 7.00(m, 2H), 3.46(s, 2H) |
| 46 | N-CH₂-(4-pyridyl) | 4-picolyl chloride·HCl | 8.52(d, J=5.94Hz, 2H), 7.26(m, overlapping, 2H), 3.52(s, 2H) |
| 47 | N-CH₂-(4-CF₃-phenyl) | 4-(trifluoromethyl)-benzyl chloride | 7.56(d, J=8.05Hz, 2H), 7.45(d, J=7.69Hz, 2H), 3.57(s, 2H) |
| 48 | N-CH₂-(4-OCH₃-phenyl) | 4-methoxybenzyl chloride | 7.25(m, overlapping, 2H), 6.85(d, J=8.63Hz, 2H), 3.79(s, 3H), 3.46(s, 2H) |
| 49 | N-CH₂-(4-OCF₃-phenyl) | 4-(trifluoromethoxy)-benzyl chloride | 7.35(d, J=8.67Hz, 2H), 7.15(m, overlapping, 2H), 3.54(s, 2H) |
| 50 | N-CH₂CH₂-P(O)(OH)₂ | Iodoethyldibenzyl phosphate | 3.27(m, 2H), 4.16(m, 2H). |
| 51 | N-CH₂-phenyl | benzyl chloride | 3.58(s, 2H), 7.28(m, 5H). |

-continued

| Ex. | N—R | Alkyl Halide | NMR |
|---|---|---|---|
| 52 | 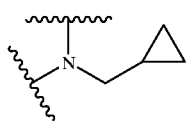 | iodomethane | (CD$_3$OD)2.2(m, 4H), 3.0(m, 1H), 3.22(s, 3H), 3.24(s, 3H), 3.6(m, 4H), 6.4(s, 1H), 7.1(m, 2H), 7.3(m, 2H), 7.4 (m, 2H), 8.3 (m, 2H) |
| 53 | 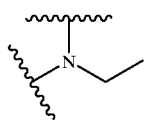 | 2,2,2-trifluoroethyl iodide | 1.8(m, 2H), 2.0(m, 2H), 2.5 (m, 2H), 2.6(m, 1H), 3.0(m, 4H), 6.2(d, J=2.9Hz, 1H), 7.0 (m, 2H), 7.2(m, 2H), 7.3 (m, 2H), 8.1(broad, 1H), 8.4 (m, 2H) |

EXAMPLE 54

To a suspension of the compound of reference example (100 mg, 0.31 mmol) and acetic acid (glacial, 0.015 ml) in anhydrous tetrahydrofuran (50 ml) under nitrogen at room temperature, cyclopropanecarboxaldehyde (0.023 ml, 0.31 mmol) and sodium triacetoxyborohydride (100 mg, 0.47 mmol) were added slowly. The resulting solution was allowed to stir at room temperature overnight. The crude product was purified by flash silica gel chromatography (MeOH—CH$_2$Cl$_2$, 8:92 v/v containing 1% NH$_4$OH). After dryness, 51 mg of the title product was obtained. NMR (CDCl$_3$) of representative peaks: 2.19(d, J=6.31 Hz, 2H), 0.97(m, 1H), 0.59(m, 2H), 0.19(m, 2H); MS(M+1)=376.1

EXAMPLE 55

Method A

To a suspension of 2-(4-fluorophenyl)-5-(piperidin-4-yl)-3-(4-pyridyl)-pyrrole (Reference Example, 1000 mg, 3.11 mmol; hereinafter referred to as Compound A) and acetic acid (0.18 ml, 3.11 mmol) in anhydrous 1,2-dichloroethane (50 ml) under nitrogen at room temperature, acetaldehyde (0.21 ml, 3.73 mmol) and sodium triacetoxyborohydride (989 mg, 4.67 mmol) were added slowly. The resulting mixture was allowed to stir for 2 hours. The crude product was purified by flash silica gel column (MeOH—CH$_2$Cl$_2$, 8:92 v/v containing 1% NH$_4$OH). After drying, 930 mg of 2-(4-fluorophenyl)-5-(N-ethylpiperidin-4-yl)-3-(4-pyridyl) pyrrole (Compound B) was obtained as the free base.

NMR (CD$_3$OD) δ 8.25(d, J=6.23 Hz, 2H), 7.34(m, 2H), 7.25(d, J=6.27 Hz, 2H), 7.09(m, 2H), 6.19(s, 1H), 3.07(d, J=11.94 Hz, 2H), 2.65(m, 1H), 2.48(qt, J=7.33 Hz, 2H), 2.11(t, J=9.95 Hz, 2H), 2.02(d, J=11.21 Hz, 2H), 1.79(m, 2H), 1.14(t, J=7.24 Hz, 3H); MS(ESI)=350.3.

Method B (Compound B diHCl Salt)

Compound A (1.0 g) in 25 ml dry methylene chloride and 10 ml of 2.5 N NaOH was cooled to 0° C. and treated with 0.25 ml of acetyl chloride dropwise. After 2 hours the solution was allowed to warm up to room temperature and stirring was continued overnight. The solution was treated with distilled water and extracted with methylene chloride. The methylene chloride layer was separated, dried over anhydrous sodium sulfate, filtered and evapotated to give 1.33 g of crude amide reaction product, which was purified by flash column (silica, methylene chloride:methanol: 25 %NH$_4$OH 90:9:1) to yield 0.7 g of 2-(4-fluorophenyl)-5-(N-acetylpiperidin-4-yl)-3-(4-pyridyl)pyrrole. This amide was dissolved in 15 ml of tetrahydrofuran and treated with 3 ml of 1M lithium aluminum hydride (LAH) in THF under an atmosphere of nitrogen at room temperature. After completion of addition of LAH, the solution was refluxed for two hours, cooled to 0° C., quenched with water (0.19 ml) and 2.5 N NaOH (0.19 ml) and filtered. The filtrate was dried over sodium sulfate, filtered, evaporated and purified by flash column as shown above to give compound B (0.65 g).

Compound B (349 mg) was suspended in 10 ml of methanol and treated with 2 ml of 1M HCl in methanol. After stirring the resulting yellow solution under nitrogen for 10 minutes, solvent was evaporated and product was kept under vacuum overnight to yield 420 mg of dihydrochloride salt of compound B.

The following compounds were prepared according to the general procedure described in Examples 54 and 55:

| Ex. | N-R | carbonyl | NMR |
|---|---|---|---|
| 56 | N-CH2-CH=C(CH3)-CH2-CH2-CH=C(CH3)2 | citral | 8.39(d, J = 5.13 Hz, 2H), 7.29(m, 2H), 7.16(d, J = 4.84 Hz, 2H), 7.02(m, 2H), 6.16(s, 1H), 5.30(m, 1H), 5.66(m, 1H), 3.12(m, 4H), 2.65(m, 1H), 2.00(m, 10H), 1.65(s, 6H), 1.58(s, 3H); MS(M + 1) = 458.3 |
| 57 | N-CH2-CH(Et)2 | 2-ethylbutanal | 8.85(s, br, 1H), 8.38(d, J = 6.18 Hz, 2H), 7.31(m, 2H), 7.17(d, J = 6.22 Hz, 2H), 7.02(m, 2H), 6.16(s, 1H), 3.16(m, 2H), 2.68(m, 1H), 2.39(d, J = 6.31 Hz, 2H), 2.20(m, 2H), 2.10(m, 2H), 2.00(m, 2H), 1.53(m, 1H), 1.37(m, 4H), 0.86(t, J = 7.32 Hz, 6H); MS(M + 1) = 466.2 |
| 58 | N-CH2-CH(CH3)-CH2-CH3 | 2-methylbutanal | 9.42(s, br, 1H), 8.38(d, J = 6.11 Hz, 2H), 7.34(m, 2H), 7.19(d, J = 6.22 Hz, 2H), 7.01(m, 2H), 6.15(s, 1H), 3.32(m, 2H), 2.75(m, 1H), 2.51(d, J = 6.96 Hz, 2H), 2.31(m, 4H), 2.00(m, 2H), 1.74(m, 1H), 1.65(m,1H), 1.45(m, 1H), 0.96(d, J = 6.67 Hz, 3H), 0.89(m, 3H); MS(M + 1) = 392.2 |
| 59 | N-CH2-CH(CH3)-CH2-CH2-CH3 | 2-methylpentanal | 8.92(s, br, 1H), 8.38(d, J = 6.14 Hz, 2H), 7.31(m, 2H), 7.18(d, J = 6.23 Hz, 2H), 7.01(m, 2H), 6.16(s, 1H), 3.20(m, 2H), 2.69(m, 1H), 2.38(m, 2H), 2.20(m, 4H), 1.98(m, 2H), 1.76(m,1H), 1.38(m, 2H), 1.25(m, 1H), 1.09(m, 1H), 0.95(d, J = 6.59 Hz, 3H), 0.88(t, J = 7.12 Hz, 3H); MS(M + 1) = 406.2 |
| 60 | N-CH2-CH2-CH(CH3)-CH2-C(CH3)3 | 3,5,5-trimethyl-hexanal | 2.00(m, 2H), 1.50(m, 2H), 1.40(m, 1H), 1.20(m, 1H), 1.07(m, 1H), 0.92(d, J = 6.31 Hz, 3H), 0.87(s, 9H); MS(M + 1) = 448.2 |
| 61 | N-CH2-(5-methylthiophen-2-yl) | 5-methyl-2-thiophenecarbox-aldehyde | 8.38(d, J = 5.98 Hz, 2H), 8.22(s, br, 1H), 7.27(m, 2H), 7.15(d, J = 6.14 Hz, 2H), 7.02(m, 2H), 6.70(d, J = 3.30 Hz, 1H), 6.58(d, J = 3.30 Hz, 1H), 6.16(s, 1H), 3.70(s, 3H), 3.05(m, 2H), 2.60(m, 1H), 2.44(s, 3H), 2.15(m, 2H),1.96(m, 2H), 1.85(m,2H); MS(M + 1) = 432.1 |
| 62 | N-cyclopentyl | cyclopentanone | 2.60(m, overlapping, 1H), 1.90(m, overlapping, 2H), 1.70(m, 2H), 1.50(m, 4H); MS(M + 1) = 390.2 |
| 63 | N-CH2-(imidazol-2-yl) | 2-imidazolecarbox-aldehyde | 8.50(s, br, 1H), 8.40(d, J = 6.19 Hz, 2H), 7.29(m, 2H), 7.16(d, J = 6.18 Hz, 2H), 7.01(m, 4H), 6.17(s, 1H), 3.79(s, 2H), 3.00(m, 2H), 2.70(m, 1H), 2.35(m, 2H), 2.00(m, 2H), 1.90(m, 2H); MS(M + 1) = 402.2 |

| Ex. | N-R | carbonyl | NMR |
|---|---|---|---|
| 64 | 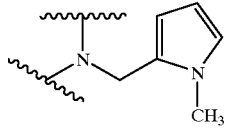 | 1-methyl-2-pyrrole-carboxyaldehyde | 8.38(d, J = 6.18 Hz, 2H), 7.28(m, 2H), 7.15(d, J = 6.22 Hz, 2H), 7.02(m, 2H), 6.60(t, J = 2.28 Hz, 1H), 6.15(s, 1H), 6.03(m, 2H), 3.65(s, 3H), 3.48(s, 2H), 2.97(m, 2H), 2.60(m, 1H), 2.07(m, 2H), 1.95(m, 2H), 1.77(m, 2H); MS(M + 1) = 415.1 |
| 65 | 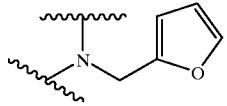 | 2-furaldehyde | 8.38(d, J = 6.18 Hz, 2H), 7.28(m, 2H), 7.15(d, J = 6.22 Hz, 2H), 7.02(m, 2H), 6.60(t, J = 2.28 Hz, 1H), 6.15(s, 1H), 6.03(m, 2H); 3.65(s, 3H), 3.48(s, 2H), 2.97(m, 2H), 2.60(m, 1H), 2.07(m, 2H), 1.95(m, 2H), 1.77(m, 2H); MS(M + 1) = 402.3 |
| 66 | 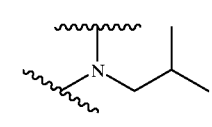 | isobutyraldehyde | 8.65(s, br, 1H), 8.38(d, J = 6.22 Hz, 2H), 7.30(m, 2H), 7.17(d, J = 6.22 Hz, 2H), 7.02(m, 2H), 6.15(s, 1H), 3.08(m, 2H), 2.65(m, 1H), 2.24(d, J = 7.28 Hz, 2H), 2.12(m, 2H), 1.99(m, 4H), 1.86(m, 1H), 0.92(d, J = 6.59 Hz, 6H); MS (M + 1) = 378.3 |
| 67 | 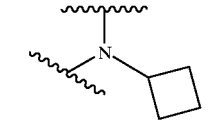 | cyclobutanone | 2.73(qn, J = 7.61 Hz, 1H), 1.80(m, overlapping, 4H), 1.70(m, overlapping, 2H); MS(M + 1) = 376.3 |
| 68 | 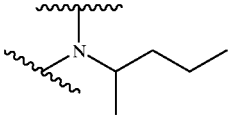 | 2-pentanone | 8.38(d, J = 6.14 Hz, 2H), 7.28(m, 2H), 7.16(d, J = 6.14 Hz, 2H), 7.02(m, 2H), 6.16(s, 1H), 2.95(m, 2H), 2.70(m, 1H), 2.62(m, 1H), 2.47(m, 1H), 2.37(m, 1H), 1.98(m, 2H), 1.88(m, 2H), 1.59(m, 1H), 1.35(m, 1H), 1.30(m, 2H), 1.04(d, 3 = 6.59 Hz, 3H), 0.91(t, J = 6.88 Hz, 3H); MS(M + 1) = 392.3 |
| 69 | 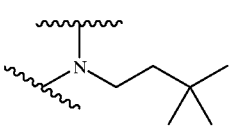 | 3,3-dimethyl-butyraldehyde | 8.41(d, J = 6.20 Hz, 2H), 8.22(s, br, 1H), 7.29(m, 2H), 7.18(d, J = 6.25 Hz, 2H), 7.04(m, 2H), 6.19(s, 1H), 3.06(m, 2H), 2.63(m, 1H), 2.41(m, 2H), 2.00(m, 2H), 1.85(m, 2H), 1.45(m, 2H), 0.92(s, 9H); MS(M + 1) = 406.4 |
| 70 | 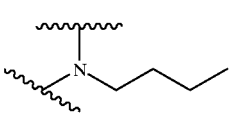 | butyraldehyde | (CD$_3$OD) 2.85(m, 2H), 1.67(m, 2H), 1.41(m, 2H), 0.99(t, J = 7.29 Hz, 3H); MS(M + 1) = 378.3 |
| 71 | 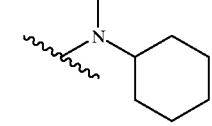 | Cyclohexanone | 1.42(m, 4H), 1.72(m, 2H), 2.16(m, 4H), 2.52(m, 1H). |
| 72 | 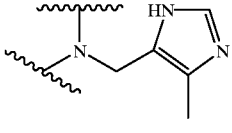 | 4-methyl-5-imidazolecarbox-aldehyde | 3.88(m, 2H), 3.56(m 3H), 7.42(s, 1H). |

-continued

| Ex. | N-R | carbonyl | NMR |
|---|---|---|---|
| 73 | 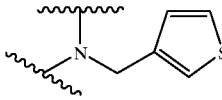 | 3-thiophenecarbox-aldehyde | 3.70(s, 2H), 7.14(m, 1H), 7.28(m, 2H). |
| 74 | 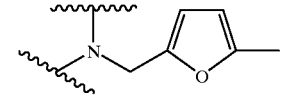 | 5-methylfurfural | 2.28(s, 3H), 5.92(d, J = 4.2 Hz, 1H), 6.20(d, J = 4.2 Hz, 1H). |
| 75 | 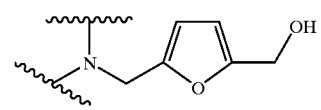 | 5-hydroxymethyl furfural | 3.76(s, 2H), 4.56(s, 2H), 6.22(d, J = 3.8 Hz, 1H), 6.32(d, J = 3.6 Hz, 1H). |
| 76 | 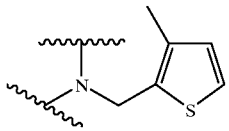 | 3-methylthiophene-2-carboxaldehyde | 2.26(s, 3H), 4.08(s, 2H), 6.88(d, J = 4.8 Hz, 1H), 7.28(d, J = 4.6 Hz, 1H). |
| 77 | 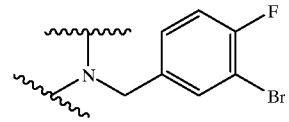 | 3-bromo-4-fluoro-benzaldehyde | 4.12(m, 2H), 7.36(m, 3H). |
| 78 | 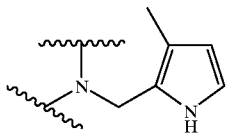 | 3-methyl-2-pyrrole-carboxaldehyde | 2.16(s, 3H), 4.08(s, 2H), 5.96(m, 1H), 6.82(m, 1H). |
| 79 | 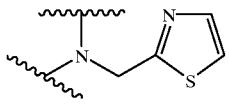 | 2-thiazolecarbox-aldehyde | 4.18(s, 2H), 7.36(d, J = 4.0 Hz, 1H), 7.76(d, J = 4.0 Hz). |
| 80 | 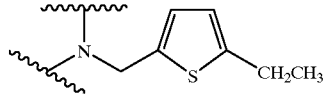 | 5-ethyl-2-thiophenecarbox-aldehyde | 3.65(s, 2H), 7.06(s, 1H), 7.66(s, 1H). |
| 81 | 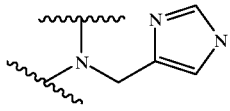 | 4(5)-imidazole-carboxaldehyde | 1.28(t, J = 8.0 Hz, 3H), 2.81(m, 2H), 3.82(s, 2H), 6.66(d, J = 3.4 Hz, 1H), 6.82(d, J = 3.5 Hz, 1H). |
| 82 | 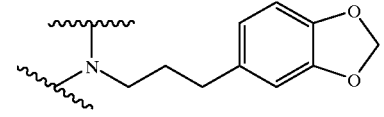 | 2-methyl-3-(3,4-methylenedioxy-phenyl)propion-aldehyde | 0.86(b, J = 6.4 Hz, 3H), 1.84(m, 2H), 2.20(m, 2H), 2.28(m, 1H), 2.72(m, 1H), 5.90(s, 2H), 6.58(dd, J = 2.2, 8.4 Hz, 1H), 6.66(d, J = 2.0 Hz, 1H), 6.72(d, J = 8.2 Hz, 1H). |
| 83 | 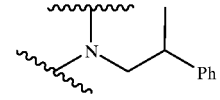 | 2-phenylpropion-aldehyde | 1.28(d, J = 6.4 Hz, 3H), 2.55(m, 3H), 7.25(m, 5H). |

-continued

| Ex. | N-R | carbonyl | NMR |
|---|---|---|---|
| 84 | 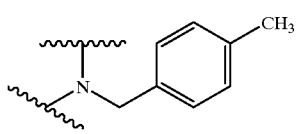 | 4-methylbenz-aldehyde | 2.0 (m, 4H), 2.4 (s, 3H), 2.7 (m, 5H), 3.5 (m, 2H), 4.0 (s, 2H), 6.2 (s, 1H), 7.0 (m, 2H), 7.2 (m, 2H), 7.3 (m, 4H), 7.4 (m, 2H), 8.4 (m, 2H) |
| 85 | 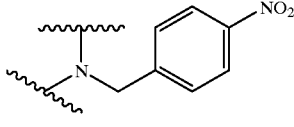 | 4-nitrobenzaldehye | 2.0 (m, 4H), 2.4 (s, 2H), 2.7 (m, 1H), 3.2 (m, 2H), 3.8 (s, 2H), 6.2 (s, 1H), 7.0 (m, 2H), 7.2 (m, 2H), 7.3 (m, 4H), 7.6 (m, 2H), 8.2 (m, 2H), 8.3 (m, 2H) |
| 86 | 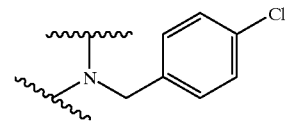 | 4-chlorobenzalde-hyde | 1.9 (m, 2H), 2.2 (m, 1H), 2.4 (m, 3H), 2.6 (m, 1H), 3.0 (m, 2H), 3.6 (s, 2H), 6.1 (s, 1H), 7.0 (m, 2H), 7.2(m, 2H), 7.3(m, 6H), 8.3 (m, 2H) |
| 87 | 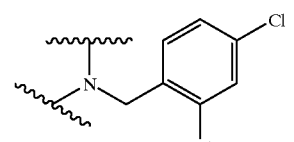 | 2,4-dichlorobenz-aldehyde | 2.0–2.5 (m, 6H), 2.8 (m, 1H), 3.2 (m, 2H), 3.8 (s, 2H), 6.2 (s, 1H), 7.0 (m, 2H), 7.2 (m, 2H), 7.3 (m, 3H), 7.4 (s, 1H), 7.7 (m, 1H), 8.4 (m, 2H), 8.8 (broad, 1H) |
| 88 | 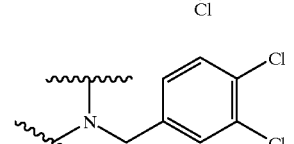 | 3,4-dichlorobenz-aldehyde | (+CD3OD)2.0 (m, 2H), 2.2 (m, 4H), 2.8 (m, 1H), 3.1 (m, 2H), 3.6 (s, 2H), 6.1 (s, 1H), 7.0 (m, 2H), 7.2 (m, 2H), 7.3 (m, 3H), 7.4 (s, 2H), 8.3 (m, 2H) |
| 89 | 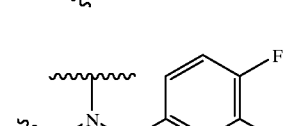 | 3,4-difluorobenz-aldehyde | (+CD3OD)2.0 (m, 2H), 2.2 (m, 4H), 2.7 (m, 1H), 3.1 (m, 2H), 3.6 (s, 2H), 6.1 (s, 1H), 7.0 (m, 2H), 7.2 (m, 4H), 7.3 (m, 3H), 8.3 (m, 2H) |
| 90 | 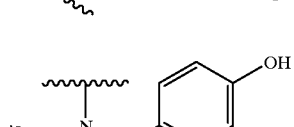 | 4-hydroxybenz-aldehyde | (+CD3OD)2.0 (m, 4H), 2.3 (m, 1H), 2.6 (m, 1H), 2.8 (m, 1H), 3.4 (m, 2H), 4.0 (s, 2H), 6.1 (s, 1H), 6.8 (m, 2H), 7.0 (m, 2H), 7.2 (m, 2H), 7.3 (m, 4H), 8.3 (m, 2H) |
| 91 | 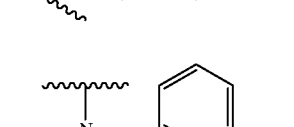 | 3-hydroxybenz-aldehyde | (+CD3OD)2.0 (m, 2H), 2.4 (m, 3H), 2.7 (m, 1H), 2.8 (m, 1H), 3.6 (m, 2H), 4.0 (s, 2H), 6.1 (s, 1H), 6.7 (m, 1H), 6.9 (m, 1H), 7.0 (m, 2H), 7.2 (m, 3H), 7.3 (m, 3H), 8.3 (m, 2H) |

General Procedure for Amide Formation

The appropriate carboxylic acid is suspended in $CH_2Cl_2$ (10 mL) at ambient temperature and hydroxybenzotriazole hydrate and triethylamine and the compound of Reference example are added. Then 1-(3-dimethylaminopropyl)-3-ethylcarbodiimide (EDC) is also added. The mixture is stirred overnight and brine and $CH_2Cl_2$ are added. The organic layer is separated, dried and concentrated.

Chromatography on Flash 40 using 9:1 methylene chloride/methanol as eluent yielded the desired amide.

General Procedure for the Reduction of Amide to Amine-Borane

The amide is dissolved in tetrahydrofuran and a borane reagent such as $BH_3$,$CH_3SCH_3$ or BH3-THF is added. The mixture is stirred for 6–16 hours at room temperature. The reaction is quenched with methanol, and the mixture concentrated to dryness. The residue is dissolved in tetrahydrofuran, and N,N-dimethylethanol-amine is added. The reaction mixture is heated under reflux for 3 hours, cooled, and evaporated to dryness. The residue is purified by preparative TLC using 90:9:1 methylene chloride/methanol/$NH_4OH$ as eluent to give the corresponding amine.

General Procedure for Lithium Aluminum Hydride Reduction

To a stirred suspension of the amide in tetrahydrofuran is added equivalent amount of lithium aluminum hydride (LAH) in tetrahydrofuran (1M) dropwise. After refluxing for 1 hour, the reaction is quenched with few drops of saturated sodium sulfate (or successive addition of ethyl acetate and drops of 15% NaOH, resuting precipate filtered), and then solvent is removed in vacuo. Purification by silica gel chromatography afforded amino products.

The following compounds were prepared in accordance with the general procedure described above.

containing 1% NH$_4$OH). After dryness, 505 mg of 2-(4-fluoro-phenyl)-5-(N-ethylpiperidin-4-yl)-3-(4-pyridyl) pyrrole N-oxide was obtained in 69% yield. NMR (CD$_3$OD) δ 8.26(d, J=6.27 Hz, 2H), 7.35(m, 2H), 7.26(d, J=6.13 Hz,

| Ex. | N-R | Reagent | NMR |
|-----|-----|---------|-----|
| 92 | | 3-(p-hydroxy-phenyl)propionic acid | (CD$_3$OD) 7.04 (m, 2H), 6.71(m, 2H), 2.90–2.64 (m, 4H) |
| 93 | | Ex. 93/ BH$_3$CH$_3$SCH$_3$ | (CD$_3$OD) 7.01(d, J = 8.60 Hz, 2H), 6.69(d, J = 8.60 Hz, 2H), 2.54(t, 7.60 Hz, 2H), 2.40(m, 2H), 1.80(m, overlapping, 2H) |
| 94 | | Cyclobutane-carboxylic acid | (CD$_3$OD) 3.44(qn, J = 8.00 Hz, 1H), 2.28(m, 2H), 2.02(m, 2H), 1.60(m, 2H) |
| 95 | | Ex. 95/LAH | (CD$_3$OD) 2.60(m, 1H), 2.48(d, J = 6.80 Hz, 2H), 2.14(m,2H), 1.77(m, 4H) |

EXAMPLE 96

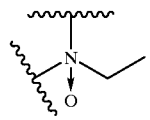

To a suspension of N-ethyl piperidine of Example 55 (700 mg, 2.0 mmol) in anhydrous dichloromethane (50 ml) under nitrogen at 0° C., 3-chloro-peroxybenzoic acid (666 mg, 2.2 mmol) was added slowly. The resulting solution was allowed to stir for 2 hours at 0° C. and for 0.5 hour at room temperature. To the resulting clear solution potassium carbonate (415 mg, 3.0 mmol) was added, and the reaction mixture was stirred for 0.75 hour. The white precipitate was removed by filtration. The crude product was purified by flash silica gel chromatography (MeOH—CH$_2$Cl$_2$, 10:90 v/v 2H), 7.11(m, 2H), 6.28(s, 1H), 3.35(m, 6H), 2.85(m, 1H), 246(m, 1H), 2.00(m, 2H), 1.39(t, J=7.10 Hz, 3H); MS(ESI)= 366.3

What is claimed is:

1. A compound of formula I

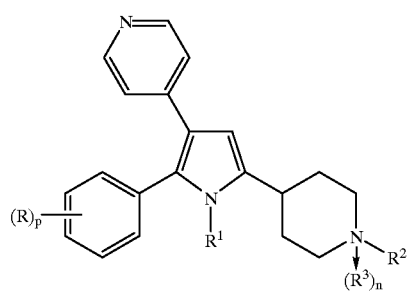

I or a physiologically acceptable salt thereof, wherein

| | |
|---|---|
| n is | 0 or 1; |
| m is | 0, 1 or 2; |
| p is | 1 or 2 or 3; |
| R is | halogen; |
| $R^1$ is | (1) hydrogen or |
| | (2) $C_{1-6}$ alkyl; |
| $R^2$ is | (1) $C_{3-12}$alkyl optionally substituted with 1 to 5 groups selected from $R^a$, |
| | (2) $C_{1-2}$alkyl substituted with 1 to 3 groups selected from $R^a$; |
| | (3) $C_{2-12}$alkenyl optionally substituted with 1 to 5 groups selected from $R^a$, |
| | (4) $C_{2-12}$alkynyl optionally substituted with 1 to 5 groups selected from $R^a$, |
| | (5) $C_{3-7}$cycloalkyl-($C_{1-6}$alkyl)$_n$, optionally substituted with 1 to 5 groups selected from $R^a$ and $C_{1-6}$alkyl, |
| | (6) aryl-($C_{1-6}$alkyl)$_n$ wherein aryl is optionally substituted with 1 to 5 groups selected from $R^b$, |
| | (7) heteroaryl-($C_{1-6}$alkyl)$_n$ wherein heteroaryl is optionally substituted with 1 to 5 groups selected from $R^b$, |
| $R^3$ is | (1) O or |
| | (2) $CH_3$; |
| $R^a$ is | (1) halogen, |
| | (2) $N_3$, |
| | (3) CN, |
| | (4) $NO_2$, or |
| | (5) $P(O)(OR^c)_2$; |
| $R^b$ is | (1) a group selected from $R^a$, |
| | (2) $C_{1-6}$alkyl optionally substituted with 1 to 6 groups selected from $R^a$, $OR^c$, $OCOR^c$, $NR^cR^c$, $NHCOR^c$, $NHSO_2R^c$, |
| | (3) aryl optionally substituted with 1 to 3 groups selected from $R^a$, $OR^c$, $OCOR^c$; $NR^cR^c$c, $NHCOR^c$, $NHSO_2R^c$, |
| | (4) heteroaryl optionally substituted with 1 to 3 groups selected from $R^a$, $OR^c$, $OCOR^c$, $NR^cR^c$c, $NHCOR^c$, $NHSO_2R^c$, |
| | (5) $C(O)OR^c$, |
| | (6) $C(O)R^c$, |
| | (7) $S(O)_mR^c$, |
| | (8) $OR^c$, |
| | (9) $OC(O)NR^cR^c$, |
| | (10) $OC(O)OR^c$, |
| | (11) $OC(O)R^c$, |
| | (12) $OSO_2R^c$ |
| | (13) $NR^cR^c$, |
| | (14) $NR^dSO_2R^c$, |
| | (15) $NR^dC(O)OR^c$, |
| | (16) $NR^dC(O)R^c$, |
| | (17) $NR^dC(O)NR^cR^c$; |
| $R^c$ is | (1) hydrogen, |
| | (2) $C_{1-2}$alkyl optionally substituted with 1 to 5 groups selected from halogen, |
| | (3) $C_{2-12}$alkenyl, |
| | (4) $C_{2-12}$alkynyl, |
| | (5) $C_{3-7}$cycloalkyl-($C_{1-6}$alkyl)$_n$, |
| | (6) aryl($C_{1-6}$alkyl)$_n$ optionally substituted with $NO_2$, $C_{1-6}$alkyl, $C_{1-6}$alkoxy, or halogen, |
| | (7) heteroaryl($C_{1-6}$alkyl)$_n$, or | two $R^c$ groups together with the nitrogen atom to which they are attached form a 3- to 7-membered ring optionally containing an additional heteroatom selected from O, S and N-$R^d$;

| | |
|---|---|
| $R^d$ is | (1) hydrogen or |
| | (2) $C_{1-6}$alkyl. | with the proviso that the following compounds are excluded: 2-(4-fluorophenyl)-5-(1-methyl-1-piperidinyl)-3-(4-pyridinyl)pyrrole, 2-(4-fluorophenyl)-5-(1-benzyl-4-piperidinyl)-3-(4-pyridinyl)pyrrole and 2-(4-fluorophenyl)-5-(1-phenyl-4-piperidinyl)-3-(4-pyridinyl)pyrrole.

2. A compound of claim 1 wherein $R^2$ is $C_{3-12}$ alkyl.

3. A compound of claim 1 wherein $R^2$ is $C_{3-6}$cycloalkyl or $C_{3-6}$cycloalkyl-$C_{1-3}$alkyl wherein said cycloalkyl is optionally substituted with 1 or 2 groups selected from $R^a$ and $C_{1-3}$alkyl.

4. A compound of claim 1 wherein $R^2$ is aryl-$C_{1-3}$alkyl wherein said aryl is substituted with 1 to 3 groups selected from $R^b$.

5. A compound of claim 1 wherein $R^2$ is heteroaryl-$C_{1-3}$alkyl wherein said heteroaryl is optionally substituted with 1 to 3 groups selected from $R^b$.

6. A compound of claim 1 having the formula Ia:

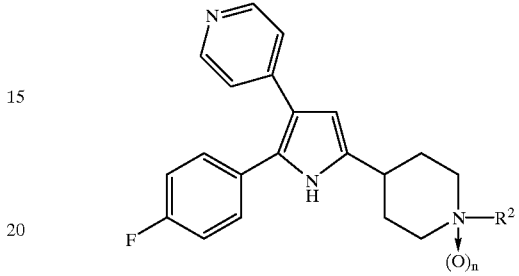

Ia wherein $R^2$ is $C_{3-12}$ alkyl, $C_{3-6}$cycloalkyl or $C_{306}$cycloalkyl-$C_{1-3}$alkyl wherein said cycloalkyl is optionally substituted with 1 or 2 groups selected from $R^a$ and $C_{1-3}$alkyl, aryl-$C_{1-3}$alkyl wherein said aryl is substituted with 1 to 3 groups selected from $R^b$, heteroaryl-$C_{1-3}$alkyl wherein said heteroaryl is optionally substituted with 1 to 3 groups selected from $R^b$.

7. A compound of claim 6 wherein $R^2$ is $C_{3-6}$ alkyl.

8. A compound of claim 6 wherein $R^2$ is $C_{3-6}$cycloalkyl or $C_{3-6}$cycloalkyl-C-1-3alkyl wherein said cycloalkyl is optionally substituted with 1 or 2 groups selected from $C_{1-3}$alkyl.

9. A compound of claim 6 wherein $R^2$ is substituted benzyl in which the substituents are one or two groups selected from halogen, $OR^c$, $OC(O)R^c$, $OC(O)NR^cR^c$, $OC(O)OR^c$, $C_{1-3}$alkyl optionally substituted with $OR^c$, $NR^cR^c$, and cyano.

10. A compound of claim 6 wherein $R^2$ is heteroarylmethyl wherein said heteroaryl is optionally substituted with 1 or 2 groups selected from $S(O)_mRf^c$, $C_{1-6}$alkyl optionally substituted with hydroxy, and halogen.

11. A compound of claim 6 wherein $R^2$ is selected from n-butyl, 2-butyl, cyclopropylmethyl, cyclobutylmethyl, 4-pyridylmethyl, 2-methyl-3-pyridylmethyl.

12. A method for the treatment or prevention of protozoal diseases comprising administering to a host in need of such treatment a therapeutically effective amount of a compound of claim 1.

13. A method for the treatment or prevention of coccidiosis in poultry comprising administering to the poultry a therapeutically effective amount of a compound of claim 1.

14. A pharmaceutical composition comprising a compound of claim 1 and an inert carrier.

15. A composition for the treatment or prevention of coccidiosis in poultry comprising a therapeutically effective amount of a compound of claim 1 in poultry feedstuff.

16. A composition of claim 15 which further comprises a second anticoccidial agent.

17. A composition of claim 16 wherein said second anticoccidial agent is selected from amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril.

* * * * *